United States Patent [19]

Matsumoto et al.

[11] Patent Number: 5,731,524
[45] Date of Patent: Mar. 24, 1998

[54] METHOD AND APPARATUS FOR MEASURING TORSIONAL RIGIDITY OF A SHAFT

[75] Inventors: Norio Matsumoto, Haramachi; Koichi Kameoka, Kakogawa, both of Japan

[73] Assignee: Fujikura Rubber Ltd., Tokyo, Japan

[21] Appl. No.: 797,299

[22] Filed: Feb. 7, 1997

[30] Foreign Application Priority Data

Feb. 13, 1996 [JP] Japan ................. 8-025669

[51] Int. Cl.$^6$ ........................... G01N 3/32
[52] U.S. Cl. ........................... 73/814; 73/650
[58] Field of Search ................. 73/814, 847, 848, 73/152.49, 649, 650, 652

[56] References Cited

U.S. PATENT DOCUMENTS

| | | | |
|---|---|---|---|
| 2,316,253 | 4/1943 | Keinath | 73/814 |
| 3,105,381 | 10/1963 | Collette | 73/847 |
| 3,112,643 | 12/1963 | Lanahan | 73/847 |
| 3,693,402 | 9/1972 | Jones | 73/814 |
| 3,772,913 | 11/1973 | Zell et al. | 73/814 |
| 3,903,734 | 9/1975 | Douglas | 73/814 |
| 3,934,459 | 1/1976 | Wolfinger et al. | 73/650 |
| 4,003,247 | 1/1977 | Moser et al. | 73/847 |
| 4,267,733 | 5/1981 | Shima et al. | 73/650 |
| 4,282,756 | 8/1981 | Molnar et al. | 73/650 |
| 4,283,957 | 8/1981 | Zobrist et al. | 73/814 |
| 4,294,120 | 10/1981 | Shima et al. | 73/650 |
| 4,715,451 | 12/1987 | Bseisu et al. | 73/152.49 |

*Primary Examiner*—Ronald L. Biegel
*Attorney, Agent, or Firm*—McCormick, Paulding & Huber

[57] ABSTRACT

A method for measuring the torsional rigidity distribution of a shaft comprises the steps of; disposing a shaft to be measured in a vertical position in which the upper end thereof is immovably held and the lower end of the shaft is rotatable about the axis of the shaft, demarcating the shaft along its length so as to establish a number of discrete sections of the shaft, performing measurements of the torsional frequency of an inertial mass held at designated discrete positions shaft, and calculating the torsional rigidity of each discrete section based on the measured torsional frequencies.

4 Claims, 5 Drawing Sheets

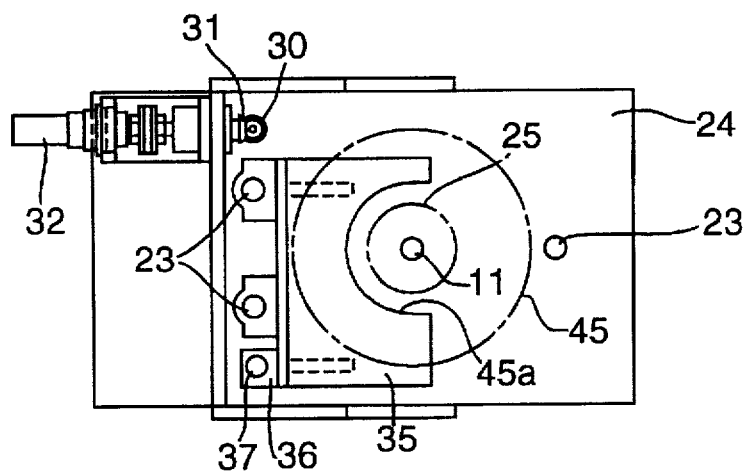
FIG. 5
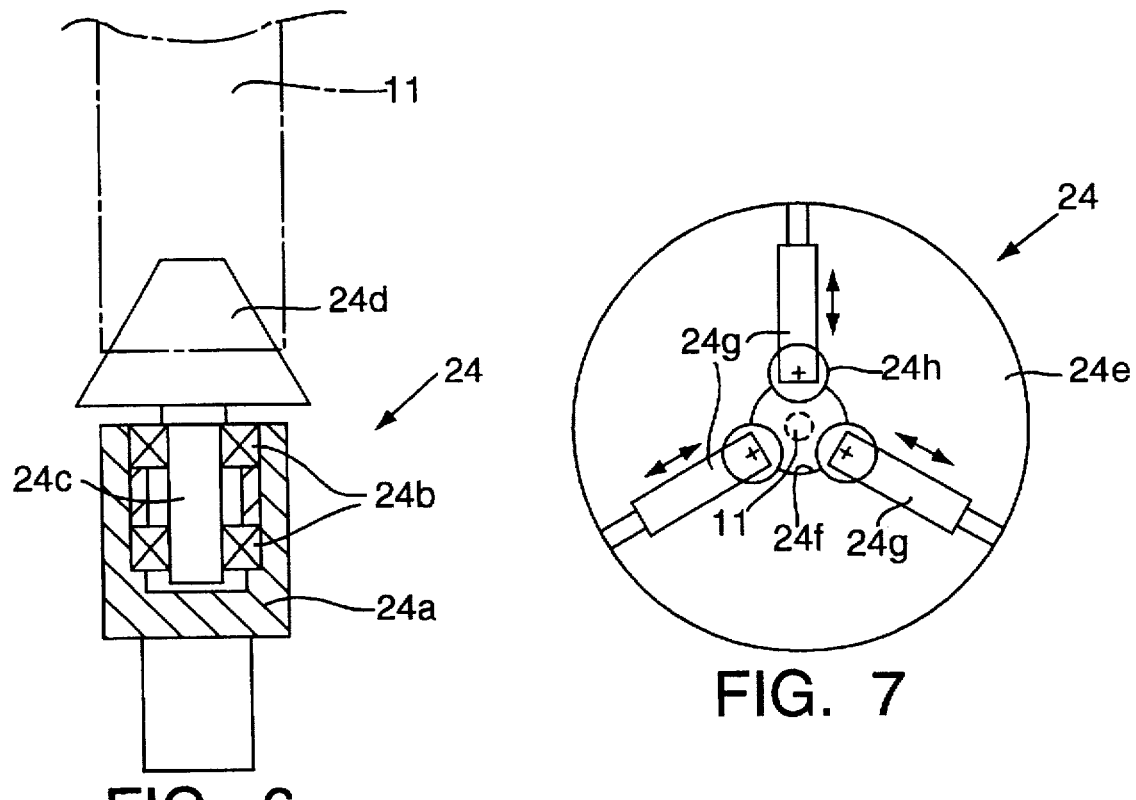
FIG. 6
FIG. 7

METHOD AND APPARATUS FOR MEASURING TORSIONAL RIGIDITY OF A SHAFT

BACKGROUND OF THE INVENTION

1. Field of the Invention

The present invention relates to a method and an apparatus for measuring torsional rigidity distribution (GIp distribution) of a shaft (rod member) along the longitudinal direction.

2. Prior Art and The Problems

To evaluate dynamic properties of a golf club shaft, various evaluation factors, such as a kick point, a bent value, or a hardness have been employed. The assignee of the present application has proposed, as a new evaluation factor, a distance $\lambda$ between a load applying point at a tip side of a shaft at which a load is being applied to deform the shaft and an intersecting point at which a tangential line at the load applying point intersects a neutral axis, as disclosed in Japanese Patent Application No. 4-42905 or Japanese Unexamined Patent Publication No. 5-35374, or a curvature distribution $1/\rho$ of a shaft when the shaft is deformed by applying a load to a point of the shaft on the tip side, as disclosed in Japanese Unexamined Patent Publication No. 4-257982 or No. 6-105934. Also, the assignee of the present application has proposed nondestructive mass distribution measuring method and apparatus for a shaft (Japanese Patent Application No. 7-27068). The new evaluation factors or measuring method mentioned above contribute to a more precise evaluation of the shaft properties and are useful to design and produce a golf club shaft suitable for an individual golfer.

OBJECT OF THE INVENTION

It is an object of the present invention to provide a method and an apparatus for measuring the torsional rigidity distribution of a shaft along the shaft length to evaluate the shaft from variously different aspect in terms of the dynamic properties. A golf club shaft has a diameter which varies in the longitudinal direction and the internal structure thereof is also different in the longitudinal direction. Therefore, it is impossible to correctly evaluate the shaft simply based on the torsional rigidity of the whole length thereof. According to the basic concept of the present invention, the torsional rigidity distribution of the shaft in the direction of the length thereof is used as a new evaluation factor.

SUMMARY OF THE INVENTION

To achieve the object mentioned above, according to the present invention, there is provided a method for measuring a torsional rigidity distribution of a shaft comprising the steps of; disposing a shaft to be measured in a vertical position in which the upper end thereof is immovably held and the lower end of the shaft is rotatable about the axis of the shaft; setting a number of discrete sections of the shaft by demarcating the shaft in the direction of the length of the shaft; discrete measuring to measure a torsional frequency of the weight that is being held at a designated discrete position by producing the torsional free oscillation on the shaft; calculating a torsional rigidity GIp of each discrete section based on the torsional frequencies measured by the discrete measurement step.

With this measuring method, the torsional rigidity distribution of a golf club shaft whose diameter and internal structure differ in the longitudinal direction thereof can be precisely detected.

The torsional frequencies can be detected by an acceleration sensor integrally provided on the weight. In an embodiment, the output of the acceleration sensor is input to a fast Fourier transformer analyzer which detects the torsional frequencies.

According to another aspect of the present invention, there is provided an apparatus for measuring a torsional rigidity distribution of a shaft comprising; a shaft chuck which immovably holds an upper end of a shaft to be measured; a bearing body which supports the lower end of the shaft to rotate about the axis of the shaft; a moving mechanism which moves one of the shaft chuck and the bearing body to come away from or close to the other; a weight which is provided with an insertion hole in which the shaft to be measured is inserted, a chuck mechanism which holds or releases the shaft inserted in the insertion hole, and an acceleration sensor; a support which is movable along the shaft to be measured and which supports or releases the weight; and, a detecting means for detecting the torsional frequency in accordance with the output of the acceleration sensor.

With this arrangement, the measuring method mentioned above can be easily carried out.

BRIEF DESCRIPTION OF THE DRAWINGS

The invention will be discussed below in detail with reference to the accompanying drawings, in which;

FIG. 5 is a plan view of an apparatus for measuring the torsional rigidity of a shaft according to an embodiment of the present invention;

FIG. 6 is a sectional view of an embodiment of a bearing portion which supports the lower end of the shaft;

FIG. 7 is a sectional view of another embodiment of a bearing portion which supports the lower end of the shaft;

PREFERRED EMBODIMENTS OF THE INVENTION

Figure 1:
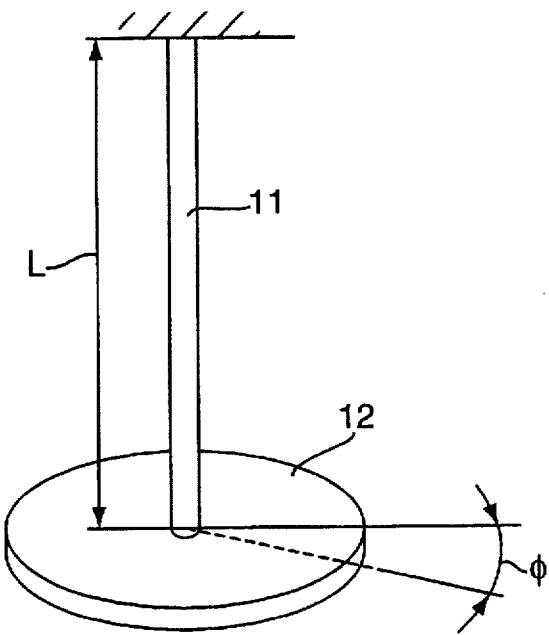
FIG. 1 is a conceptual view to explain an equation of a free oscillation for the rotation of a disc secured to a shaft.

The principle of measurement of an equivalent torsional rigidity of the whole length of a shaft will be discussed below with reference to FIG. 1 which shows an embodiment of the present invention. It is assumed that a shaft 11 whose length is L is fixed at the upper end and is provided at the lower end with a weight 12 in the form of a circular disc, secured thereto. If an initial torsion is applied to the weight 12 and is released thereafter, the shaft 11 and the weight 12 vibrate. The free vibration of the shaft 11 and the weight 12 with respect to the rotation $\psi$ is given by the following equation (1);

$$J(d^2\psi/dt^2)=-K\cdot\psi \quad (1)$$

wherein

J: moment of inertia of the disc-shaped weight 12 with respect to the center axis (Nm²)

K: equivalent torsion spring constant of the shaft 11 (i.e., torque Nm/rad necessary to twist the shaft of length L by 1 rad.)

The following equation (2) from the equation (1) is obtained;

$$(d^2\psi/dt^2)+\omega^2\cdot\omega=0 \quad (2)$$

wherein $$\omega: \text{natural (circular) frequency (rad/sec} =(K/J)^{1/2}) \quad (3)$$

The natural (cyclic) frequency f is represented by $$f=\omega/2\pi=(1/2\pi)(K/J)^{1/2} (Hz) \quad (4)$$

The relationship between the equivalent torsion spring constant K and the equivalent torsional rigidity $GI_p$ is specified by $$K=GI_p/L \quad (5)$$

Therefor, the equivalent torsional rigidity $GI_p$ is given by $$GI_p=4\pi^2\cdot L\cdot J\cdot f^2 \quad (6)$$

In the equation (6), L and J are predetermined values inherent to the shaft 11 and the disc-shaped weight 12. Thus, the equivalent torsional rigidity $GI_p$ of the shaft 11 through the entire length thereof can be obtained by measuring the value of f.

In the calculation mentioned above, the moment of inertia of the shaft 11 is neglected. If the disc-shaped weight 12 whose moment of inertia is remarkably larger than that of the shaft 11, the equivalent torsional rigidity Glp obtained would be sufficiently practicable.

Figure 2:
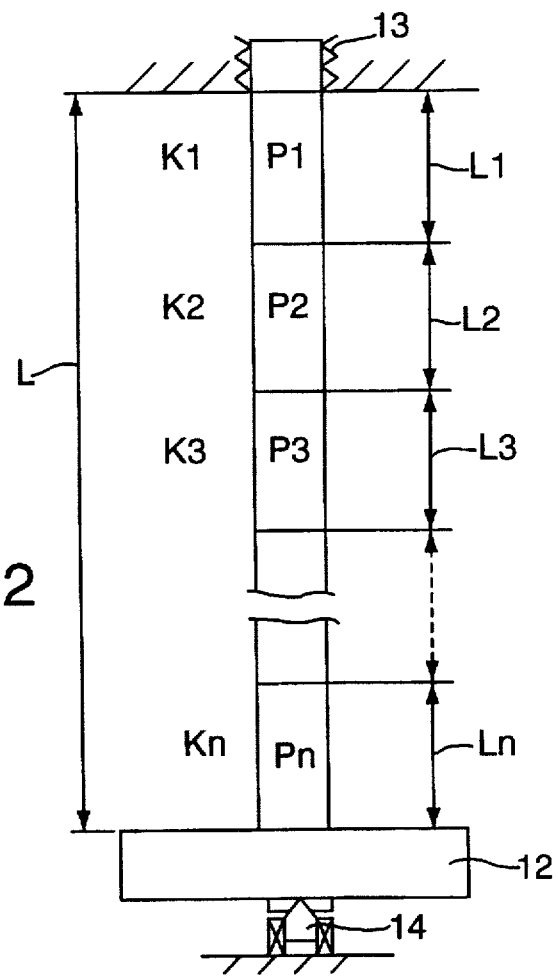
FIG. 2 is a conceptual view to explain the principle of the measurement of a torsional rigidity of a shaft according to the present invention.
Figure 3:
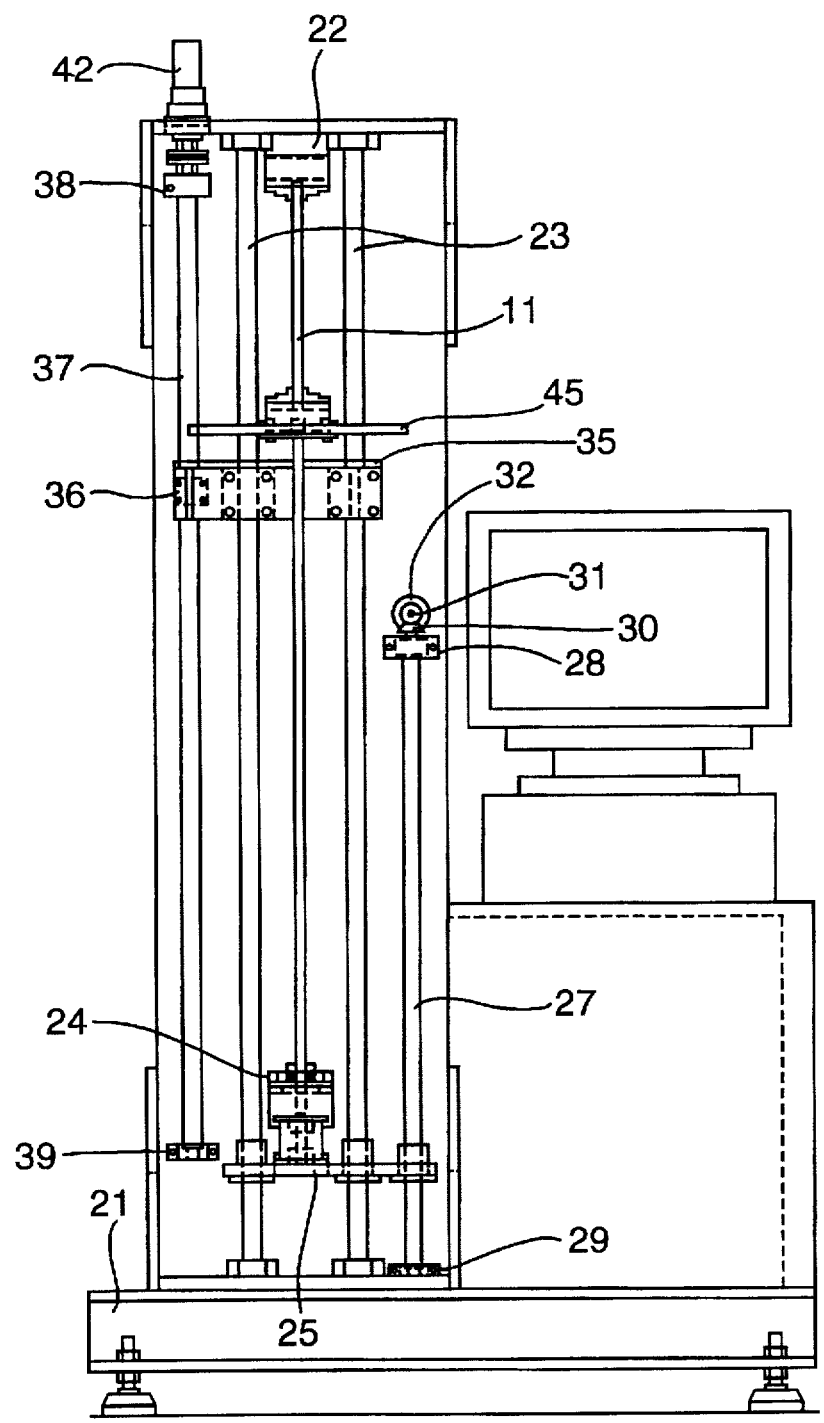
FIG. 3 is a front elevational view of an apparatus for measuring the torsional rigidity of a shaft according to an embodiment of the present invention.
Figure 4:
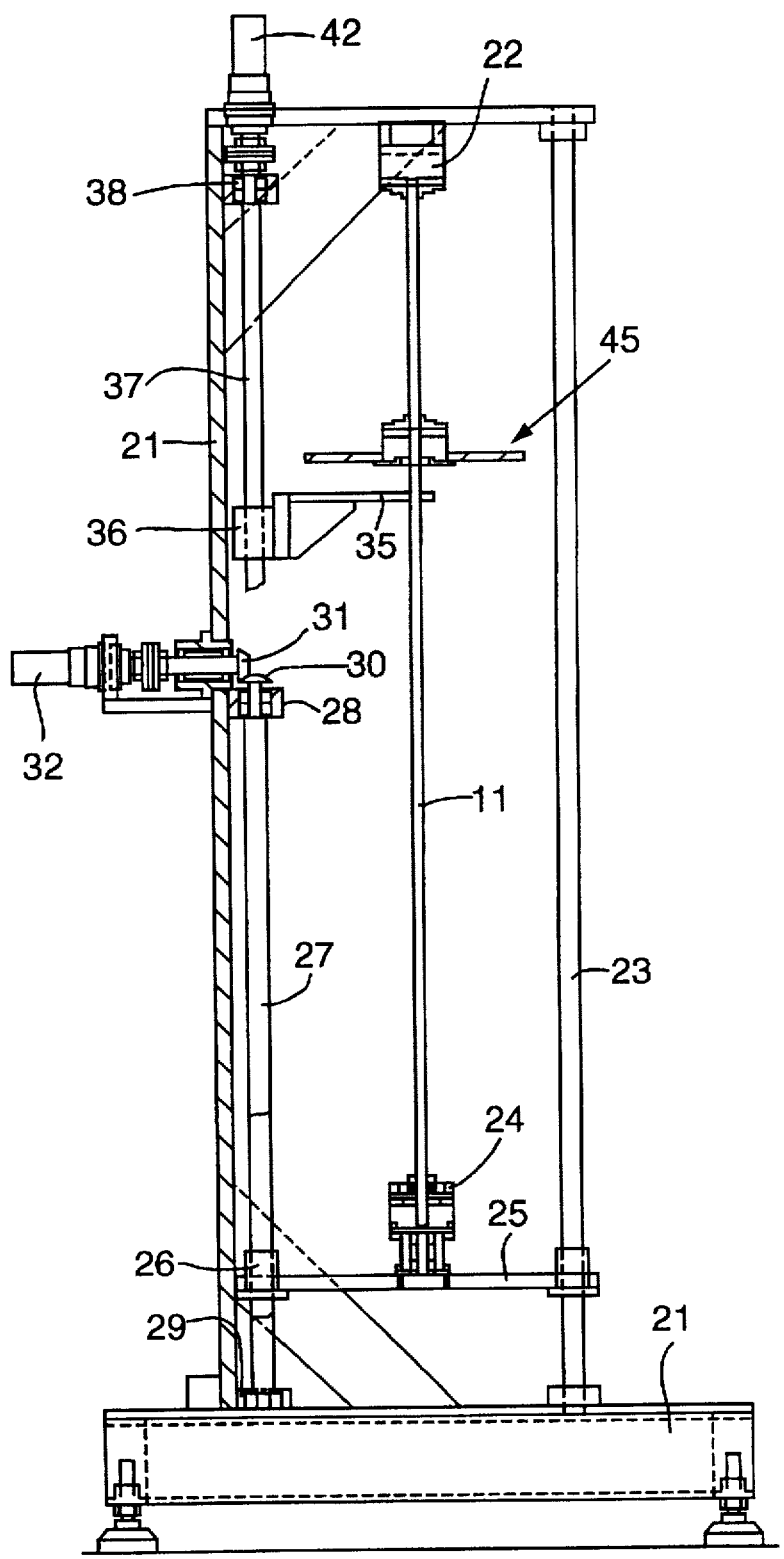
FIG. 4 is a side elevational view of an apparatus for measuring the torsional rigidity of a shaft according to an embodiment of the present invention.

The principle of measurement according to the present invention will be discussed below with reference to FIG. 2.

In general, the diameter of the golf club shaft is not uniform in the direction of the length thereof, and the internal structure is not identical in the longitudinal direction, as mentioned above. Therefore, it is impossible to precisely evaluate the shaft, based only on the torsional rigidity along the whole length thereof.

To this end, according to the present invention, the torsional rigidity distribution of the shaft 11 in the longitudinal direction thereof is obtained and used as a new evaluation factor by the following steps;

Step A (FIG. 2): The shaft 11 is disposed in a vertical position and the upper end thereof is secured. The lower end of the shaft 11 is rotatable about the axis of the shaft.

Step B: The discrete components (sections) P1 (length $L_1$), P2 (length $L_2$), P3 (length $L_3$), ... Pn (length $L_n$) are defined in the longitudinal direction in this order from the upper end.

Step (discrete measurement step) C: The disc-shaped weight 12 is attached to each of the discrete components P1, P2, P3 .... Pn and is, for example, struck to produce a torsional rigidity of the shaft 11 and the weight 12. The torsion frequency of the weight 12 is then measured for each section P1, P2, P3 ... Pn.

Step D: The value of $GI_p$ of each discrete component is calculated, based on the torsion frequencies measured at the discrete measurement step.

The upper end of the shaft 11 is secured by means of a shaft chuck 13 and the lower end of the shaft 11 is supported, for example, by a bearing body 14 so as to rotate about the axis of the shaft 11.

The calculation is carried out as follows.

Under the condition that the spring constants of the discrete sections P1, P2, P3, ... Pn are K1, K2, K3, ... Kn, respectively, the resultant spring constant K of the shaft 11 is given by;

$$1/K=(1/K_1)+(1/K_2)+(1/K_3)\ldots(1/K_n) \quad (7)$$

From equations (5) and (7), we have the following equation (8) which represents the relationship between the torsional rigidity $GI_p$ of the whole length of the shaft and the torsional rigidity $GI_{pi}$ of the split sections;

$$L/GI_p=(L_1/GI_{p1})+(L_2/GI_{p2})+(L_3/GI_{p3})+\ldots(L_n/GI_{pn}) \quad (8)$$

From the equation (8), an equation (9) below is obtained.

$$L_i/GI_{pi}=(L_{1\cdot i}/GI_{p1\cdot i})-(L_{1\cdot(i-1)}/GI_{p1\cdot(i-1)}) \{i=2,3\ldots,n\} \quad (9)$$

Therefore, $$GI_{pi}=L_i\{(L_{1\cdot i}/GI_{p1\cdot i})-(L_{1\cdot(i-1)}/GI_{p1\cdot(i-1)})\}^{-1} \quad (10)$$

wherein $L_{1\cdot(i-n)}$: total length of the shaft 11 from the split sections P1 to (Pn−1)

$GI_{p1\cdot(i-1)}$: evaluated torsional rigidity of the shaft 11 from the discrete sections P1 to (Pn−1).

$GI_{p1\cdot i}$ and $GI_{p1\cdot(i-1)}$ are expressed as follows from the equation (7);

$$GI_{p1\cdot i}=4\pi^2 JL_{1\cdot i}(f_{1\cdot i})^2 \quad (11)$$

$$GI_{p1\cdot(i-1)}=4\pi^2 JL_{1\cdot(i-1)}(f_{1\cdot(i-1)})^2 \quad (12)$$

Using the equations (11) and (12), the equation (10), the following equation (13) is obtained:

$$GI_{p\cdot i}=4\pi^2 JL_i\{1/(f_{1\cdot i})^2\}-\{1/(f_{1\cdot(i-1)})^2\}\}^{-1}$$

$$i=2,3,\ldots,n \quad (13)$$

wherein $f_{1\cdot i}$: natural frequency of the shaft having the weight at the lower end of the discrete section i $f_{1\cdot(i-1)}$: natural frequency of the shaft having the weight at the lower end of the split section (i−1)

The equation (13) is used to obtain the torsional rigidity of an optional section (i=2~n), i.e., the torsional rigidity distribution by using the measurement of the natural frequency.

By sliding the weight along the length of the shaft and securing the weight to the shaft at an optional position, the value of $GI_{p\cdot i}$ (i=2~n) can be obtained by carrying out the following steps;

step 1: $f_{1\cdot n}$ is measured when the weight is secured to the shaft at a position spaced by a distance $L_{1\cdot n}$ from the secured upper end of the shaft.

step 2: $f_{1\cdot(n-1)}$ is measured when the weight is moved upward and secured to the shaft at a position spaced by a distance $L_{1\cdot(n-n)}$ from the secured upper end of the shaft.

step 3: $f_{1\cdot(n-2)}$ through $f_{1\cdot 1}$ are measured successively when the weight is successively moved upward.

step 4: $GI_{p\cdot i}$ is calculated by the equation (13) using the values of $f_{1\cdot 1}$ through $f_{1\cdot n}$ thus measured.

The torsional rigidity can be obtained in accordance with the frequency inherent thereto, using an acceleration sensor (pickup) attached to the disc-shape weight 12, wherein the output of the acceleration sensor is input to an FFT analyzer (Fast Fourier Transformer).

The measuring process mentioned above can be equally applied to the measurement of the flexural rigidity of the shaft 11. Namely, the flexural rigidity distribution through the whole length of the shaft 11 can be obtained by replacing the torsional rigidity $GI_p$ with flexural rigidity EI. In this measurement, there is no support of the shaft 11 at the lower end thereof by the bearing 14. The bending frequency is detected using the acceleration sensor and the FFT analyzer. The bending frequency thus obtained is interpolated in the equation (13) in which "coefficient 4", "J", and "$L_i$" are replaced with 4/3, the mass of the weight, and $L_{i3}$, respectively.

The measuring apparatus which carries out the measuring method mentioned above will be discussed below with reference to FIGS. 3 to 8. A shaft chuck 22 is secured to a body frame 21 at the upper end thereof. The shaft chuck 22 which detachably holds the shaft 11 can be of any type, for example, a chuck of a lathe.

Three upright guide rails 23 are secured to the body frame 21. A bearing plate 25 which carries a bearing body 24 is supported by the guide rails 23 to move up and down. The bearing body 24 is provided with an internal thread body (female screw) 26 which engages with a feed screw shaft 27 which extends in parallel with the guide rails 23. The feed screw shaft 27 is rotatably supported at the upper and lower ends thereof by respective bearings 28 and 29 secured to the body frame 21. The feed screw shaft 27 is provided on the upper end thereof with a bevel gear 30. The body frame 21 is provided with a motor 32 with a reduction gear, having a bevel gear 31 which is in mesh with the bevel gear 30. Thus, when the motor 32 with a reduction gear is rotated in the forward or reverse direction, the feed screw shaft 27 is rotated in the forward or reverse direction to move the bearing plate 25 up or down.

The bearing body 24 supports the shaft 11 at the lower end thereof so as to rotate the shaft 11 about the axis thereof. Although the internal structure of the bearing body 24 does not matter in the present invention, FIGS. 6 and 7 show two examples thereof. FIG. 6 shows an internal support type in which the shaft 11 is supported at the inner periphery. In FIG. 6, a rotating upright shaft 24c is held by a stationary member 24a secured to the bearing plate 25 through roller bearings 24b. The upright shaft 24c is provided on the upper end thereof with a cone (tapered member) 24d, integral therewith, which can be inserted in the axial bore of the shaft 11. With this arrangement, when the cone 24d is inserted and fitted in the central bore of the shaft 11 (inner diameter portion) which extends from and is held by the shaft chuck 22 by moving the bearing plate 25 in the upward direction, the shaft 11 can rotate without being bent.

FIG. 7 shows an external support type in which the shaft 11 is supported at the outer periphery thereof. In FIG. 7, a stationary disc 24e secured to the bearing plate 25 carries three chuck bodies 24h which are movable in the radial direction from the center hole 24f of the disc 24e. The chuck bodies 24g are provided on the front ends thereof with rotatable roller bearings. The chuck bodies 24g are moved synchronously with each other through a synchronization mechanism (not shown) similar to that in a lathe. With this arrangement, the bearing plate 25 is moved upward, so that the shaft 11 which extends from and is held by the shaft chuck 22 enters the central hole 24f of the bearing plate. In this state, the bearing bodies 24g are moved toward the shaft 11 to bring the roller bearings 24h into contact with the shaft 11, so that the shaft 11 can be rotatably held without being bent.

Two of the three guide rails 23 carry a weight support plate 35 which is always located above the bearing plate 25 to move up and down. The weight support plate 35 is provided with an internal thread body 36 which is screw-engaged by the feed screw shaft 37 extending in parallel with the guide rails 23. The feed screw shaft 37 is rotatably supported at the upper and lower ends thereof by bearings 38 and 39 secured to the frame body 21. The feed screw shaft 37 is directly connected at the upper end thereof to an encoder motor 42 with a reduction gear secured to the frame body 21. Consequently, when the encoder motor 42 is rotated in the forward or reverse direction, the feed screw shaft 37 is rotated in the forward or reverse direction to move the weight support plate 35 up or down. The encoder motor 42 can precisely control the axial position of the weight support plate 35 in the direction of the length of the feed screw shaft. The discrete sections of the shaft 11 are set in accordance with the axial position of the weight support plate 35.

Figure 8:
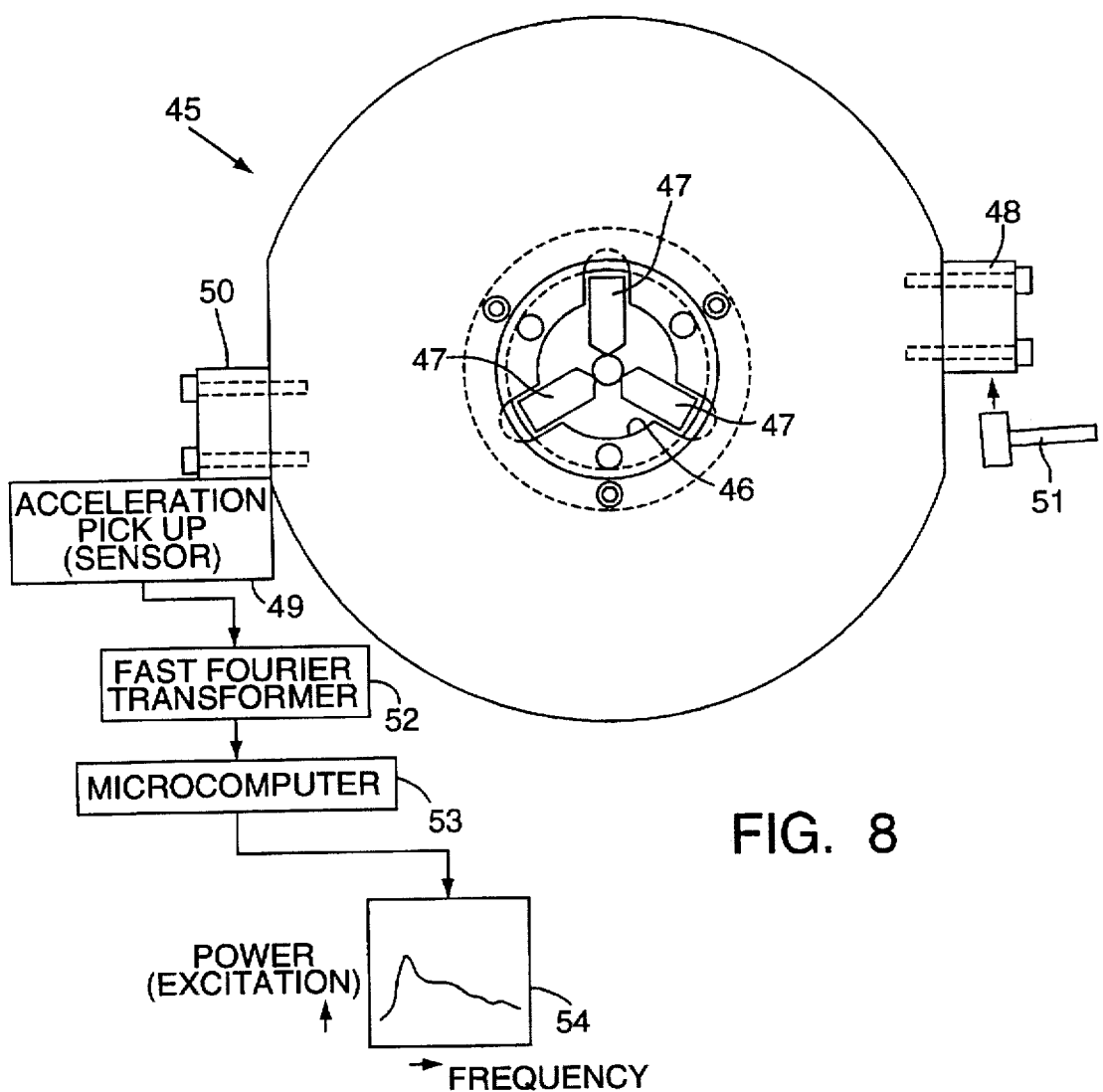
FIG. 8 is a schematic plan view of a disc-shaped weight and an acceleration pickup unit connected thereto; and, FIG. 9 is a graph showing a torsional rigidity distribution of a golf club shaft, measured by measuring apparatus and method according to the present invention, by way of example.

The weight support plate 35 carries the weight 45 in the form of a circular disc on the upper surface thereof. The disc-like weight 45 is provided with a center hole (shaft insertion hole) 46, and a chuck mechanism which holds and releases the shaft 11 inserted in the center hole 46. When the shaft 11 is released, the weight 45 is moved upward together with the weight support plate 35 and when the shaft 11 is held by the chuck mechanism, the weight support plate 35 is only moved downward. FIG. 8 shows an example of the disc weight 45 which is of rotation-symmetry with respect to the center hole 46 in which the shaft 11 is inserted. There are three chucking jaws 47 in the center hole 46 to move in the radial directions. When the chucking jaws 47 are synchronously moved toward the center of the weight, the shaft 11 can be held by the chucking jaws at the center of the weight. When the chucking jaws are moved in opposite directions, the shaft 11 is released. For example, a chuck mechanism for a lathe can be used for the mechanism to move the chucking jaws 47. The weight support plate 35 is provided with a recess 45a (FIG. 5) which supports the lower surface of the weight 45 but permits the shaft 11 and the bearing plate 25 to pass therethrough.

The disc weight 45 is provided with an vibrating projection 48 and a mounting projection 50 for the acceleration pickup (sensor) 49 in a rotation symmetry arrangement with respect to the center hole 46. The vibrating projection 48 projects in the radial direction so as to produce an vibration in the torsional direction by an vibrating hammer 51 (or to reduce the vibration components other than the torsional vibration). The output of the acceleration pickup 49 is sent to the FFT analyzer 52 so that the torsional frequency can be detected through the microcomputer 53 and is indicated on the display 54.

The apparatus constructed as above operates as follows.

The upper end of the shaft 11 is immovably held by the shaft chuck 22, and the bearing plate 25 is elevated by the motor 32 with a reduction gear, so that the lower end of the shaft 11 is rotatably supported by the bearing body 24. After the weight support plate 35 is moved to the lowermost position, i.e., below the n-th discrete section of the shaft 11, the weight support plate 35 is moved upward by a predetermined length of the discrete sections. In this position, the disc weight 45 is connected to the shaft 11 by means of the chucking jaws 47 and the weight support plate. 35 is moved downward. Namely, the support of the disc weight 45 is released, and then, the excitation projection 48 is struck by the hammer 51 to produce a torsional vibration on the disc weight 45 and the shaft 11. The torsional frequency is detected through the acceleration pickup 49, the FFT analyzer 52 and the microcomputer 53 and is displayed in the display 54.

When the measurement of the torsional frequency of the first split section of the shaft is complete, the weight support plate 35 is moved upward by the encoder motor 42 to support the lower surface of the disc weight 45. Thereafter, the chucking of the shaft 11 by the chucking jaws 47 is released. Thereafter, the weight support plate 35 (and the disc weight 45) is elevated by the encoder motor 42 by a predetermined length of the second discrete sections. This operation is repeated until the measurement of the torsional frequencies of all the split sections of the shaft is completed.

Figure 9:
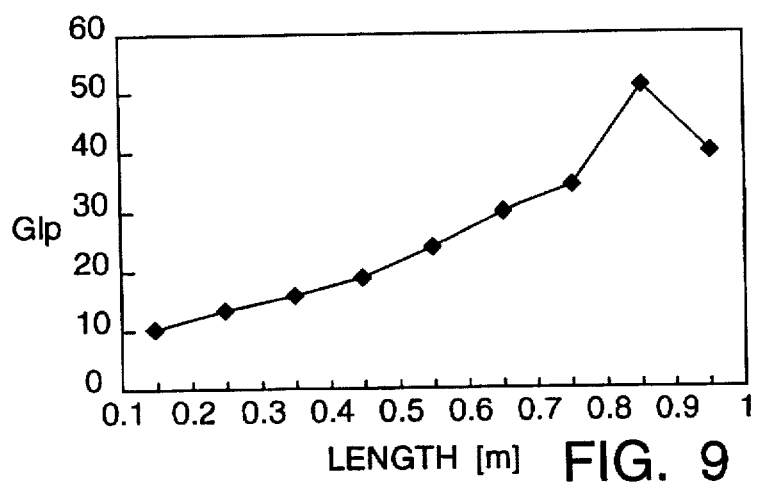

In the measurements mentioned above, since the natural torsional frequencies f1i of the split sections P1, P2 . . . Pn are measured, the torsional rigidity distribution ($GI_p$ distribution) of the whole length of the shaft 11 can be obtained by calculating the measured values. FIG. 9 shows a graph of the calculation result by way of example. The number of the discrete sections can be increased as many as possible. As the number of the discrete sections increases, the precision in the measurement of the torsional rigidity distribution ($GI_p$ distribution) increases.

Although the above discussion has been applied to the golf club shaft, the present invention can be equally applied to measure the torsional rigidity distribution of other shafts, for example, a stick for ski.

EFFECT OF THE INVENTION

According to the present invention, the torsional rigidity distribution of a shaft can be measured, which can be used as a new evaluation factor of a shaft.

What is claimed is:

1. A method for measuring a torsional rigidity distribution of a shaft; comprising the steps of;

disposing a shaft to be measured in a vertical position, so as to have upper and lower ends and a vertical longitudinal axis, with said upper end of the shaft being immovably held and with said lower end of the shaft being rotatable about said longitudinal axis of the shaft, providing a weight movable vertically relative to the shaft along said longitudinal axis of said shaft;

defining a number of discrete longitudinal sections of the shaft, attaching said weight in turn to the shaft at each of said discrete longitudinal sections of the shaft;

measuring the torsional frequency at which said weight freely vibrates about said longitudinal axis of said shaft when said weight is attached to each of said discrete longitudinal sections of said shaft; and calculating a torsional rigidity GIp of each of said discrete longitudinal sections of said shaft based on the torsional frequencies measured during said measuring step.

2. A method for measuring a torsional rigidity distribution of a shaft according to claim 1, wherein the torsional frequencies are detected by an acceleration sensor integrally provided on the weight.

3. A method for measuring a torsional rigidity distribution of a shaft according to claim 2, wherein the output of the acceleration sensor is input to a fast Fourier transformer analyzer which detects the torsional frequencies.

4. An apparatus for measuring a torsional rigidity distribution of a shaft oriented vertically so as to have upper and lower ends and a vertical longitudinal axis, said apparatus comprising;

a shaft chuck which immovably holds said upper end of the shaft to be measured;

a bearing body which supports said lower end of the shaft to rotate about said longitudinal axis of the shaft;

a moving mechanism which moves one of the shaft chuck and the bearing body to come away from or toward the other;

a weight having an insertion hole through which the shaft to be measured is inserted, a chuck mechanism which holds or releases the shaft inserted in the insertion hole, and an acceleration sensor;

a support which is movable vertically along the shaft to be measured and which supports or releases the weight to allow the weight to be moved vertically relative to the shaft and to be fixed by said chuck mechanism in turn to said shaft at a number of different positions along said longitudinal axis; and, a detecting means for detecting the torsional frequency in accordance with the output of the acceleration sensor.

* * * * *